(12) United States Patent
Wang

(10) Patent No.: US 9,415,073 B2
(45) Date of Patent: *Aug. 16, 2016

(54) SOMATIC STEM CELLS

(71) Applicant: StemBios Technologies, Inc., Monterey Park, CA (US)

(72) Inventor: James Wang, Monterey Park, CA (US)

(73) Assignee: Stembios Technologies, Inc., Montery Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/740,816

(22) Filed: Jun. 16, 2015

(65) Prior Publication Data

US 2015/0342997 A1 Dec. 3, 2015

Related U.S. Application Data

(60) Continuation of application No. 13/895,733, filed on May 16, 2013, now Pat. No. 9,072,719, which is a division of application No. 13/366,906, filed on Feb. 6, 2012, now Pat. No. 8,679,474, which is a continuation-in-part of application No. 13/198,181, filed on Aug. 4, 2011, now Pat. No. 8,623,642.

(60) Provisional application No. 61/370,600, filed on Aug. 4, 2010, provisional application No. 61/383,842, filed on Sep. 17, 2010, provisional application No. 61/446,669, filed on Feb. 25, 2011.

(51) Int. Cl.
| | | |
|---|---|---|
| *C12N 5/077* | (2010.01) |
| *A61K 35/28* | (2015.01) |
| *A61K 9/00* | (2006.01) |
| *A61K 39/00* | (2006.01) |
| *C12N 5/0784* | (2010.01) |
| *G01N 33/50* | (2006.01) |
| *A61K 35/14* | (2015.01) |
| *A61K 35/15* | (2015.01) |
| *A61K 35/12* | (2015.01) |

(52) U.S. Cl.
CPC ............ *A61K 35/28* (2013.01); *A61K 9/0019* (2013.01); *A61K 35/14* (2013.01); *A61K 35/15* (2013.01); *A61K 39/0011* (2013.01); *C12N 5/0639* (2013.01); *C12N 5/0652* (2013.01); *G01N 33/5091* (2013.01); *A61K 2035/124* (2013.01); *A61K 2039/5154* (2013.01); *C12N 2500/10* (2013.01); *C12N 2501/11* (2013.01); *C12N 2501/115* (2013.01); *C12N 2501/125* (2013.01); *C12N 2501/135* (2013.01); *C12N 2501/22* (2013.01); *C12N 2501/2303* (2013.01); *C12N 2501/91* (2013.01); *C12N 2506/00* (2013.01); *C12N 2506/03* (2013.01)

(58) Field of Classification Search
CPC ... A61K 35/28; A61K 9/0019; C12N 5/0652; C12N 5/0658; C12N 2506/03; C12N 2506/1346
See application file for complete search history.

(56) References Cited

U.S. PATENT DOCUMENTS

| | | |
|---|---|---|
| 6,004,807 A | 12/1999 | Banchereau et al. |
| 6,440,735 B1 | 8/2002 | Gaeta |
| 6,716,422 B1 | 4/2004 | Gajewski et al. |
| 7,575,921 B2 | 8/2009 | Vacanti et al. |
| 7,972,847 B2 | 7/2011 | Kalinski |
| 8,158,758 B2 | 4/2012 | Gurney |
| 8,673,296 B2 | 3/2014 | Karlsson-Parra et al. |
| 2004/0136967 A1 | 7/2004 | Weiss et al. |
| 2004/0175823 A1 | 9/2004 | Vacanti et al. |
| 2006/0040392 A1 | 2/2006 | Collins et al. |
| 2009/0004661 A1 | 1/2009 | Shetty |
| 2009/0104158 A1 | 4/2009 | Young et al. |
| 2009/0104160 A1 | 4/2009 | Young et al. |
| 2009/0155225 A1 | 6/2009 | Ratajczak et al. |
| 2009/0186334 A1 | 7/2009 | Young et al. |
| 2010/0081199 A1 | 4/2010 | Slukvin et al. |
| 2012/0021482 A1 | 1/2012 | Zuba-Surma et al. |
| 2012/0028355 A1 | 2/2012 | Sato et al. |
| 2012/0034194 A1 | 2/2012 | Wang |

FOREIGN PATENT DOCUMENTS

| | | |
|---|---|---|
| WO | WO-2009/012357 | 1/2009 |
| WO | WO-2009/059032 | 5/2009 |
| WO | WO-2009/061024 | 5/2009 |
| WO | WO-2009/136283 | 11/2009 |
| WO | WO-2010/039241 | 4/2010 |
| WO | WO-2010/083203 | 7/2010 |
| WO | WO-2012/019002 | 2/2012 |

OTHER PUBLICATIONS

Aiuti, et al., "Expression of CXCR4, the Receptor for Stromal Cell-derived Factor-1 on Fetal and Adult Human Lympho-hematopoietic Progenitors", European Journal of Immunology. Published 1999. Wiley-VCH Verlag GmbH, Weinheim. pp. 1823-1831.
Aoyama et al. "Stromal cell CD9 regulates differentiation of hematopoietic stem/progenitor cells" Hematopoiesis, Blood, 93(8):2586-2594, 1999.
Banerjee et al. "An antibody to the tetraspan membrane protein CD9 promotes neurite formation in a partially $\alpha 3\beta 1$ integrin-dependent manner" The Journal of Neuroscience 17(8):2756-2765, 1997.
Barker, et al., "Identification of stem cells in small intestine and colon by marker gene Lgr5", Articles, Nature Publishing Group, Oct. 2007.
Barker, et al., "Lgr5+ve Stem Cells Drive Self-Renewal in the Stomach and Build Long-Lived Gastric Units in Vitro", Cell Stem Cell, vol. 6, Jan. 2010.

(Continued)

*Primary Examiner* — Daniel C Gamett
(74) *Attorney, Agent, or Firm* — Cesari and McKenna LLP

(57) ABSTRACT

Described herein is a method of generating muscle cells in a subject. The method includes isolating a population of somatic stem cells that are CD133− and 0.3-6.0 micrometers in size and administering to a subject in need thereof an effective amount of the somatic stem cells, whereby the somatic stem cells differentiate into muscle cells in the subject.

17 Claims, 6 Drawing Sheets

(56) References Cited

OTHER PUBLICATIONS

Battula, et al. "Prospective isolation and characterization of mesenchymal stem cells from human placenta using a frizzled-9-specific monoclonal antibody", Differentiation, 2008, vol. 76, pp. 326-336.
Battula, et al., "Human placenta and bone marrow derived MSC cultured in serum-free, b-FGF-containing medium express cell surface frizzled-9 and SSEA-4 and give rise to multilinelage differentiation", Differentiation, Spinger Verlag, DE, col. 75, No. 4, Apr. 2007.
Bellato, et al., Pain Research and Treatment vol. 2012 pp. 1-7.
Buhring et al. "Novel markers for the prospective isolation of human MSC" Ann. N.Y. Acad. Sci. 1106:262-271, 2007.
Cai, et al., (NeuroMolecular Medicine, 2002, vol. 2, pp. 233-249).
Cui et al. "Spatial distribution and initial changes of SSEA-1 and other cell adhesion-related molecules on mouse embryonic stem cells before and during differentiation" Journal of Histochemistry & Cytochemistry, 52(11):1447-1457, 2004.
Fickert et al. "Identification of subpopulations with characteristics of mesenchymal progenitor cells from human osteoarthritic cartilage using triple staining for cell surface markers" Arthritis Research & Therapy, 6(5):R422-R432, 2004.
Furusawa et al. "Embryonic stem cells expressing both platelet endothelial cell adhesion molecule-1 and stage-specific embryonic antigen-1 differentiate predominantly into epiblast cells in a chimeric embryo" Biology of Reproduction, 70:1452-1457 (2004).
Gang et al. Prospective isolation of MSC with SSEA-4; Blood First Edition Paper, prepublished on line Oct. 24, 2006: DOI 10.1182/blood-2005-11-010504.
Gang et al. "SSEA-4 identifies mesenchymal stem cells from bone marrow", Stem Cells in Hematology, Blood, 109(4):1743-1751, 2007.
Glazar et al. "IgSF8 (EWI-2) and CD9 in fertilization: Evidence of distinct functions for CD9 and a CD9-associated protein in mammalian sperm-egg interaction" Reprod Fertil Dev. 21(2):293-303, 2009.
Huang et al. "Isolation and characterization of cell subpopulation with stem cell properties in human and monkey intervertebral disc (IVD)" EMC Journal 2009 p. 28.
Hung, et al., "Isolation and characterization of size-sieved stem cells from human bone marrow", Stem Cells, Alphamed Press, vol. 20, No. 3, 2002.
Hur, "Highly Angiogenic CXCR4 and CD31 monocyte subset derived from 3D culture of human peripheral blood", Biomaterials, 2013, pp. 1929-1941.
Jaks, et al, "Lgr5 marks cycling, yet long-lived, hair follicle stem cells," Nature Genetics, vol. 40, No. 11, 1291-1299 (2008).
Kadam et al. "Islet neogenesis from the constitutively nestin expressing human umbilical cord matrix derived mesenchmal stem cells" Islets 2:2, 112-120, 2010.
Kim et al. "Role of CD9 in proliferation and proangiogenic action of human adipose-derived mesenchymal stem cells" Cell and Molecular Physiology Eur. J. Physiol 455:283-296, 2007.
Kim, et al., "Generation of human induced pluripotent stem cells from osteoarthritis patient-derived synovial cells", Arthritis and Rheumatism, 6(10):3010-2021 (2011).
Kogler, et al., "A new human somatic stem cell from placental cord blood with intrinsic pluripotent differentiation potential", Journal of Experimental Medicine, vol. 200, No. 2, 2004.
Kucia et al. "Evidence that very small embryonic like (VSEL) stem cells are mobilized into peripheral blood" Stem Cells Express, published online Jun. 5, 2008; doi:10.1634/stemcells.2007-0922 p. 1-23.
Kucia, et al., "A population of very small embryonic-like (VSEL) CXCR4+SSEA=1+Oct4+ stem cells identified in adult bone marrow", Leukemia, vol. 20, 2006.
Kucia, et al., "Morphological and molecular characterization of novel population of CXCR4+ SSEA=4+ very small embryonic-like cell purified from human cord blood—preliminary report", Leukemia, vol. 21, 2007.
Kucia, et al., "Physiological and pathological consequences of identification of very small embryonic like (VSEL) stem cells in adult bone marrow", Journal of Physiology and Pharmacology, 2006, 57, Supp 5, 5-18.
Lian et al. "Establishing clonal cell lines with endothelial-like potential from CD9hi, SSEA-1 Cells in embryonic stem cell-derived embryoid bodies" PLoS One 1:(e6)1-10, 2006.
Lindvall, et al., J. Clin Invest. Jan. 4, 2010; 120(1): 29-40.
Magnus, et al., Philos Trans R Soc Lond B Biol Sci. Jan. 12, 2008; 363 (1489): 9-22.
Meng et al. "Endometrial regenerative cells: A novel stem cell population" Journal of Translational Medicine, 5:(57)1-10, 2007.
Meregalli, et al., BioDrugs 2010, vol. 24, Issue 4, pp. 237-247.
Muller et al. "A novel embryonic stem cell like derived from the common marmoset monkey (*Callithrix jacchus*) exhibiting germ cell-like characteristics" Human Reproduction, 24(6):1359-1372, 2009.
Negroni, et al., Expert Opin Biol Ter. Feb. 2011; 11(2):157-176.
Noggle, et al., "Notch signaling is inactive but inducible in human embryonic stem cells", Stem Cells, vol. 24, No. 7, 2006.
Oka et al. "CD9 is associated with leukemia inhibitory factor-mediated maintenance of embryonic stem cells" Molecular Biology of the Cell, 13:1274-1281, 2002.
Prowse et al. "Multiplexed staining of live human embryonic stem cells for flow cytometric analysis of pluripotency markers" Stem Cells and Development, 18(8): 1135-1139, 2009.
Ratajczak, et al., "Very small embryonic-like (VSEL) stem cells: purification from adult organs, characterization, and biological significance", Stem Cell Reviews, vol. 4, No. 2, 2008.
Sackstein, et al., "Ex vivo glycan engineering on cd44 programs human multipotent mesenchymal stromal cell trafficking to bone", Nat. Med., vol. 14, pp. 181-187, 2008.
Sato, et al., "Paneth cells constitute the niche for Lgr5 stem cells in intestinal crypts", Nature, vol. 469, Jan. 2011.
Shinohara et al. "CD9 is a surface marker on mouse and rat male germline stem cells", Biology of Reproduction, 70:70-75, 2004.
Shmilovici "Mammalian spore-like cells—A reservoir of spare parts for old-age?" Medical Hypotheses, 2007, 68:767-769.
Stout et al. "Primitive stem cells residing in the skeletal muscle of adult pigs are mobilized into the peripheral blood after trauma" The American Surgeon, 73:1106-1110, 2007.
Tole et al. "Distribution of CD9 in the developing and mature rat nervous system" Developmental dynamics 197:94-106, 1993.
Tourandre, et al., Arthritis & Rheumatism vol. 64, No. 2, pp. 533-541, 2012.
Trubiani et al. "Expression profile of the embryonic markers nanog. OCT-4, SSEA-1, SSEA-4 , and frizzled-9 receptor in human periodontal ligament mesenchymal stem cells" 2010 DOI.10.1002/jcp.22203p. 1-14.
Vacanti et al. "Identification and initial characterization of spore-like cells in adult mammals" Journal of Cellular Biochemistry, 80:455-460, 2001.
Wojakowski et al "Very Small Embryonic-Like Stem Cells in Cardiovascular Repair" Pharmacology & Therapeutics vol. 129, pp. 21-28. 2011.
Young "Existence of Reserve quiescent stem cells in adults, from amphibians to humans" Immunol., 280:71-109, 2004.
Young et al. "Cancer gene mechanisms and gene therapy" Reviews, Minerva Biotec. 17:55-63, 2005.
Yu, et al., Liver Transpl. Jan. 2012; 18 (1): 9-21.
Zuba-Surma, et al., "'Small stem cells' in adult tissues: Very small embryonic-like stem cells stand upl", Cytometry Part A, vol. 75A, No. 1, 2009.
Zulewski et al. "Multipotential nestin-positive stem cells isolated from adult pancreatic islets differentiate ex vivo into pancreatic endocrine, exocrine, and hepatic phenotypes" Diabetes, 50:521-533, 2001.

SEQUENCE LISTING

```
<160> NUMBER OF SEQ ID NOS: 66

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
agctgaacgg gaagctcact                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
tgctgtagcc aaattcgttg                                              20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ctcaccctgg gggttctatt                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 4
ctccaggttg cctctcactc                                              20

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
catgagtgtg gatccagctt g                                            21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
cctgaataag cagatccatg g                                            21

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
tcggcgccgg ggagatacat                                              20

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
cccccggcgg caatagca                                                18

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
tgcaccagac cagtgcaaac attc                                         24

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
acttggctgc tgtcactttc atgc                                         24

<210> SEQ ID NO 11
<211> LENGTH: 24
```

```
<212> TYPE: DNA
<213> ORGANISM: Artificial sequence
<220> FEATURE:
<223> OTHER INFORMATION: Synthetic oligonucleotide

<400> SEQUENCE: 11
tgatgagctg actgggcttt gcta                                              24

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 12
tgaccatgag cttctccagc ttct                                              24

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ccattgtcca cgccaccaac                                                   20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tgagtgcatg ctgggcagag                                                   20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
gagtcaacgg atttggtcgt                                                   20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ttgattttgg agggatctcg                                                   20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
```
ttatctcacc ccttccttgg                                          20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gccatcatgt agcattcctg                                          20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
tgtgagtggc cccgaccctg                                          20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
acgattgtgg cgacggctcc                                          20

<210> SEQ ID NO 21
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 21
tcgaagaagg tgtgggcaga aga                                      23

<210> SEQ ID NO 22
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 22
atttcctgag acttgctggc ctct                                     24

<210> SEQ ID NO 23
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 23
tgtgaaacac aagcccaagg ca                                       22

<210> SEQ ID NO 24
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 24
ccctcctcgg caaagcaggt                                               20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ggttgggagc tgatgaaact                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gaatagggct ggaacaagga                                               20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
caggcttcgg ctcaggcacc                                               20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
atcggggccg ggtgacttca                                               20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
agcgatcaag gagaccaaag                                               20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
aagcacagag ggtcattgag                                               20
```

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
gttggctgaa aaggtggtct                                              20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
cacaaccacc cacaagtcat                                              20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
gctcaaggaa cccaagagag                                              20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
ggcaccaagt cttccaattt                                              20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
cgcacaccag gcactcctgg                                              20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
cacctggcct gtggcggatg                                              20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 37
tgcccggcac tggggactta                                          20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
tagcgggcca ggcctctcag                                          20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ctccagcaca gcccaggtgc                                          20

<210> SEQ ID NO 40
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 40
tgctggcttc cttggcatca tgc                                      23

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aagatcggct ccactgagaa                                          20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ggacgtgggt gatattgtcc                                          20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
agcctttgtg aaccaacacc                                          20

<210> SEQ ID NO 44
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
gctggtagag ggagcagatg                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gaggccacta agtgccagag                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
ttcttcacca cagcaacagc                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
aaatgcgttt ctcgttgctt                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
gccacaggcc aatagtttgt                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
cactagccag gtctcgaagg                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
```

```
ctgaggacca gaagcacctc                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
gctcaggagc tatgcctcac                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
acctagccaa tggcactcag                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
aagtcagacc aagccgaaga                                               20

<210> SEQ ID NO 54
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 54
gcacaggaga cttgcctttt                                               19

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
gctggagtcc tcacagaagg                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
tctccagctc atgcacattc                                               20

<210> SEQ ID NO 57
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 57
ttcagtgctg accagattgc                                                  20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
aaatggcttg catcataggc                                                  20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
tgagagccct cacactcctc                                                  20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
tcagccaact cgtcacagtc                                                  20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
cgactccgga tgtagagaaa                                                  20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
ttcccgaact tgattctgag                                                  20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
cagtgccatc cagtacatcg                                                  20
```

```
<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
aggttgtggg catctgtagg                                              20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
tgattctgag caagctggtg                                              20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
cggtagtgcc catcattctt                                              20
```

SOMATIC STEM CELLS

RELATED APPLICATIONS

This application is a continuation of U.S. application Ser. No. 13/895,733, filed on May 16, 2013, which is a division of U.S. application Ser. No. 13/366,906, filed on Feb. 6, 2012, now U.S. Pat. No. 8,679,474, which is a continuation-in-part of U.S. application Ser. No. 13/198,181, filed on Aug. 4, 2011, now U.S. Pat. No. 8,623,642, which claims priority to U.S. Provisional Application No. 61/370,600, filed on Aug. 4, 2010; U.S. Provisional Application No. 61/383,842, filed on Sep. 17, 2010; and U.S. Provisional Application No. 61/446,669, filed on Feb. 25, 2011. The contents of the prior applications are incorporated herein by reference in their entirety.

BACKGROUND

Stem cells are pluripotent or totipotent cells that can differentiate in vivo or in vitro into many or all cell lineages. Due to their pluripotency, embryonic stem (ES) cells are believed to hold a great promise for treating degenerative or inherited diseases. Yet, ethical considerations have hampered the use of human ES cells. Stem cells of a non-embryonic origin would circumvent this obstacle. Thus, there is a need for non-embryonic stem cells.

SUMMARY

This invention relates to somatic stem cells, either pluripotent or totipotent, and related methods.

One aspect of this invention features an isolated somatic stem cell that is 0.3-6.0 micrometer in size (e.g., 0.3-5.0, 0.3-4.0, and 0.3-3.0 micrometers in size) and is CD9+. The isolated somatic stem cell can be CD9+CD349+ or CD9+ CD349−. The sign "+" following a cell marker stands for a higher fluorescent staining with a marker-specific antibody, as compared to a lower fluorescent staining with an isotype control of the antibody. The sign "−" following a cell marker stands for the same fluorescent staining with a marker-specific antibody as that with an isotype control of the antibody. In one embodiment, the isolated somatic stem cell is non-adherent. This cell is named "SB-1 cell" herein.

In another aspect, this invention features an isolated somatic stem cell that is 0.3-6.0 micrometer in size (e.g., 0.3-5.0, 0.3-4.0, and 0.3-3.0 micrometers in size) and is SSEA1+, SSEA4+, CD13+, or Stro1+. In one embodiment, the isolated somatic stem cell is non-adherent. This cell is named "SB-2 cell" herein.

In still another aspect, the invention features a method of preparing a population of somatic stem cells. The method includes obtaining from a subject (e.g., a human or non-human) a bodily fluid sample (e.g., blood, bone marrow, umbilical cord blood, menstrual fluid, and amniotic fluid) containing a plurality of cells, incubating the sample with a divalent cation chelating agent (e.g., EDTA, EGTA, and sodium citrate) or heparin in a container until the sample is separated into an upper layer and a lower layer, collecting the upper layer, and isolating from the upper layer a population of somatic stem cells that are 0.3-6.0 micrometers in size (e.g., 0.3-5.0, 0.3-4.0, and 0.3-3.0 micrometers in size). The cell population in the upper layer is named "SB cells" or "a SB cell population" herein.

The somatic stem cells in the SB cell population can be CD9+, SSEA1+, SSEA4+, CD13+, or Stro1+. For example, they can be CD9+CD349+. These somatic stem cells are not adherent cells and can have both morphological and growth characteristics of a zygote cell. Further, they can be induced to form all three germ layers, i.e., endoderm, ectoderm, and mesoderm.

The isolation of SB cells from the upper layer can be conducted by methods based on cell sizes (e.g., centrifuging and filtering) or those based on cell surface markers (e.g., flow cytometry).

The method can further include, after the upper layer has been collected, incubating it with ADP so as to allow platelets/microparticles to precipitate for further enrichment of the stem cells. In addition, it can also include incubating the upper layer obtained from a heparin-treated sample with a divalent cation chelating agent to activate the cell cycle of the stem cells from G0 into G1.

In a further aspect, the invention features the SB cell population prepared by the method described above.

In a yet another aspect, the invention features a cell bank including a plurality of populations of somatic stem cells. The populations are separately prepared from bodily fluid samples, e.g., blood and bone marrow, from different subjects by the above-described method.

The invention further features a method of increasing the number of stem cells contained in a sample. The method includes adding a divalent cation chelating agent to the sample and incubating the stem cells in the sample with the divalent cation chelating agent. The method can further include determining the counts of the cells of interest (e.g., SB-1 cells, SB-2 cells, and both SB-1 cells and SB2 cells) in the sample both before addition of a chelating agent and after incubation of the cells with the chelating agent. Examples of the stem cells to be tested by this method include stem cells in a SB population, e.g., SB-1 cells.

Also within the scope of this invention is a method of evaluating a subject for a risk of having an ageing-related disorder or cancer. The examples of the ageing-related disorder include a self-repair defect, a degenerative disease, an autoimmune disease, a cardiovascular disease, and diabetes. The method includes obtaining a population of certain somatic stem cells from a subject and determining the count of the somatic stem cells. The obtained somatic stem cells can be SB-1 cells or SB-2 cells. They can be CD9+, CD349+, SSEA1+, SSEA4+, CD13+, or Stro1+. They are each 0.3-6.0 micrometer in size. Stem cells in a SB population can be obtained by the method described above, preferably using heparin for separation of a bodily fluid sample into an upper layer and a lower layer.

The subject is determined to have a risk of having the disorder if the count is below a first predetermined value or to have a risk of having cancer if the count is above a second predetermined value. The first value can be obtained from a first control subject that is young and healthy. The second value can be obtained from a second control subject that has cancer.

The invention also includes a method for increasing the number of somatic stem cells in a subject. This method includes administering to a subject in need thereof an effective amount of the somatic stem cells in a SB cell population. The respective counts of the cells of interest (such as SB-1 cells) both before and after the administration can be determined in samples (e.g., blood and bone marrow) from the subject. As an example, to practice this method, somatic stem cells in 250 ml of a phosphate buffer containing 10 nM-5 μM EDTA can be used.

Finally, the invention features a method for treating a muscle injury or a muscle-degenerative disease. The method includes administering to a subject in need thereof an effective amount of the somatic stem cells in a SB cell population.

Examples of the muscle-degenerative disease include muscular dystrophy, fibromyalgia, myopathies, dermatomyositis, polymyositis, rhabdomyolysis, and myocarditis.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
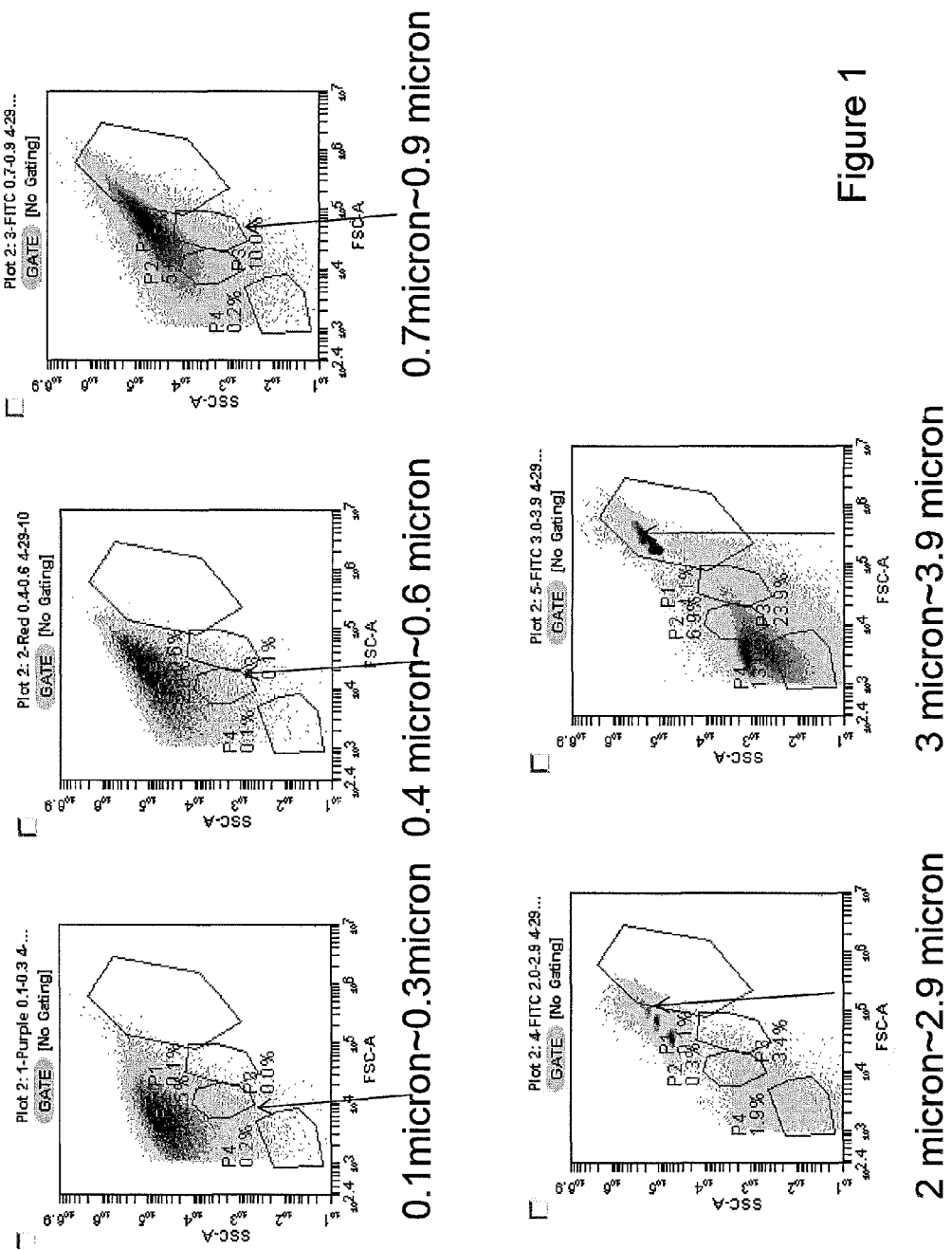
FIG. 1 includes five scatter plots showing sizes of standard beads used to estimate the sizes of cells in the P1-gated region.

This invention is based, at least in part, on the unexpected discoveries (i) that a pluripotent or totipotent stem cell population, i.e., a SB cell population, can be isolated from a sample that was believed to contain no cells, (ii) that a divalent cation chelating agent (e.g., EDTA) activates pluripotent or totipotent stem cells in this population and forces them to proliferate without losing their differentiation potentials; and (iii) that this population of pluripotent or totipotent stem cells can be differentiated to ectoderm, endoderm, and mesoderm cells. SB-1 cells in this population is stained positive for CD9 and SB-2 cells in it is stained positive for one or more of SSEA1+, SSEA4+, CD13+, and Stro1+. The SB cell population, SB-1 cells, and SB-2 cells can be isolated either from a human or from a non-human. Below are examples of a non-human, from which the above-mentioned somatic stem cells can be obtained: primate, dog, rodent, guinea pigs, cat, horse, cow, sheep, and pig. In other words, they include, but are not limited to, pet animals, farm animals, experimental animals, and disease-model animals.

A. Cells

This invention relates to a SB cell population, a population of pluripotent or totipotent stem cells prepared from non-embryonic origins. Like ES cells, cells in this population are totipotent or pluripotent. More importantly, this population can be obtained easily at a very high yield. It therefore can be used to regenerate differentiated, functional cells in treating various degenerative disorders or tissue damage. As shown in the examples below, the population can be easily prepared, maintained, and expanded in vitro, and induced to differentiation using routine technical approaches. In addition, after grafting the stem cells in the population into an animal subject (e.g., a mouse), there is no evidence of malignant growth. Containing a normal chromosomal complement, these stem cells are lineage-uncommitted and can form all somatic (non-reproductive) cells of the body. They can also form the reproductive gametes sperm and/or ovum, and cells and tissues of the embryonic and fetal portions of the placenta. These stem cells are responsive to lineage-induction agents, proliferation agents, and differentiation inhibitory agents. Due to these advantages, they represent an alternative to other stem cells.

The term "stem cell" herein refers to a cell that is totipotent or pluripotent, i.e., capable of differentiating into a number of final, differentiated cell types. Totipotent stem cells typically have the capacity to develop into any cell type. Totipotent stem cells can be both embryonic and non-embryonic in origin. Pluripotent cells are typically cells capable of differentiating into several different, final differentiated cell types. Unipotent stem cells can produce only one cell type, but have the property of self-renewal which distinguishes them from non-stem cells. These stem cells can originate from various tissue or organ systems, including blood, nerve, muscle, skin, gut, bone, kidney, liver, pancreas, thymus, and the like.

The stem cells disclosed herein are substantially pure. The term "substantially pure", when used in reference to stem cells or cells derived therefrom (e.g., differentiated cells), means that the specified cells constitute the majority of cells in the preparation (i.e., more than 20%, 30%, 40%, 50%, 60%, 70%, 80%, 90%, or 95%). Generally, a substantially purified population of cells constitutes at least about 70% of the cells in a preparation, usually about 80% of the cells in a preparation, and particularly at least about 90% of the cells in a preparation (e.g., 95%, 97%, 99% or 100%). As such, a method of the invention provides the advantage that a substantially pure population of a particular type of cells (e.g., SB-1 cells) can be obtained without contamination by other cell types.

Various cell-containing samples from a subject can be used to prepare the cell population of this invention. In a preferred embodiment of this invention, the cell population is prepared from a blood or bone marrow sample.

To confirm that this isolated population indeed contains SB-1 cells, one can examine a number of characteristics, including (1) sizes of cells in suspension that between 0.3 to 6.0 µm, preferably 0.5 to 5.0 µm, and (2) cell surface markers. Antibodies against cell surface markers, such as CD9, can be used. They can be conjugated with suitable labels, such as fluorescein isothiocyanate (FITC), phycoerythrin (PE), or quantum dots. SB-1 cells, which are CD+, can be further enriched using flow cytometry.

The isolated or enriched cells are then tested by standard techniques. To confirm the differentiation potential of stem cells in the SB cell population, they can be induced to form, for example, neuro-glial cells, osteocyte, and adipocyte by methods known in the art. For example, these cells can be passed and cultured to confluence, shifted to an osteogenic medium or an adipogenic medium, and incubated for suitable time (e.g., 3 weeks). The differentiation potential for osteogenesis is assessed by the mineralization of calcium accumulation, which can be visualized by von Kossa staining. To examine adipogenic differentiation, intracellular lipid droplets can be stained by Oil Red O and observed under a microscope. For neural differentiation, these cells can be incubated in a neurogenic medium for suitable duration (e.g., 7 days), and then subjected to serum depletion and incubation of β-mercaptoethanol. After differentiation, they exhibit the morphology of refractile cell body with extended neuritelike structures arranged into a network. RT PCR and immunocytochemical stain of lineage specific markers are further conducted to confirm neural differentiation. Examples of the markers include neuron specific class III β-tubulin (Tuj-1), neurofilament, and GFAP.

Alternatively, to confirm the identity of the isolated cells, one can take advantage of the discovery that SB-1 cells, in response to a divalent cation chelating agent (EDTA), proliferate quickly. To that end, one can culture the isolated cells with, e.g., EDTA. Under that condition, SB-1 cells will proliferate. In contrast, CD66e$^+$ cells do not behave similarly.

Stem cells in a SB cell population can be further propagated in a non-differentiating medium culture for more than 10, 20, 50, or 100 population doublings without indications of spontaneous differentiation, senescence, morphological changes, increased growth rate, or changes in ability to differentiate into neurons. These stem cells can be stored by standard methods before use.

The terms "proliferation" and "expansion" as used interchangeably herein with reference to cells, refer to an increase in the number of cells of the same type by division. The term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. Differentiation may be assessed, for example, by monitoring the presence or absence of lineage markers, using immunohistochemistry or other procedures known to a worker skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

The terms "lineage commitment" and "specification," as used interchangeably herein, refer to the process a stem cell undergoes in which the stem cell gives rise to a progenitor cell committed to forming a particular limited range of differentiated cell types. Committed progenitor cells are often capable of self-renewal or cell division.

The term "terminal differentiation" refers to the final differentiation of a cell into a mature, fully differentiated cell. For example, neural progenitor cells and muscle progenitor cells can differentiate into hematopoietic cell lineages, terminal differentiation of which leads to mature blood cells of a specific cell type. Usually, terminal differentiation is associated with withdrawal from the cell cycle and cessation of proliferation. The term "progenitor cell," as used herein, refers to a cell that is committed to a particular cell lineage and which gives rise to cells of this lineage by a series of cell divisions. An example of a progenitor cell would be a myoblast, which is capable of differentiation to only one type of cell, but is itself not fully mature or fully differentiated.

Within the scope of this invention is a cell bank or library having a plurality of above-described populations of stem cells. These stem cells can be human cells or non-human cells. The bank can be produced by harvesting SB cell populations separately from different subjects; characterizing the SB cell populations to obtain at least one predetermined characteristic for each, and cataloguing each of the SB cell populations according to the at least one predetermined characteristic. To produce the bank, one can further expand the SB cell populations. Examples of the characteristic include a subject's name, gender, physical conditions (including genetic disorders and MHC information)

B. Use of Cells:

The above-described SB cell population, containing, e.g., SB-1 cells, can be used in a variety of ways.

Screening Methods:

The above-described stem cells in a SB cell population can be used in screening assays to identify drugs that can affect a particular cell type in a manner indicating that the drug can be useful for treating a disorder associated with the cell type. For example, one can use the stem cells in a method for identifying a drug candidate for treating a disease (e.g., a degenerative disease). The method includes the steps of contacting a test compound with the stem cells and determining the expression level of a polypeptide that is down-regulated in the disease. The expression level in the presence of the test compound, if higher than that in the absence of the compound, indicates that the compound is a candidate for treating the disease. Examples of the disease include diabetes, a neurodegenerative disease, arthritis, cancer, or an autoimmune disorder. The expression level can be determined at either the mRNA level or at the protein level.

Thus, one aspect of the present invention relates to a method for identifying an agent that alters a function of an undifferentiated cell in a SB cell population by contacting the cells with a test agent. A change in a function or gene expression of the cells in presence of the test agent as compared to the function in the absence of the test agent indicates that the test agent is an agent that alters the function of or the gene expression in the cells. The term "test agent" refers to any molecule that is being examined for an ability to alter a function of or gene expression in the cells. Although the method generally is used as a screening assay to identify previously unknown molecules that have a desired activity, the screening methods of the invention also can be used to confirm that an agent known to have a particular activity.

The function can be expression of gene that typically is expressed (or not expressed) in the cells, and the agent can alter the function by increasing or decreasing the level of expression of an expressed gene, or by turning on the expression of an unexpressed gene (e.g., inducing expression of lineage-specific antigen) in the cells.

In one embodiment, the agent that affects a function of the cells is one that induces differentiation of stem cells, thereby producing differentiated cells. Such differentiated cells can be multipotential human stem cells (e.g., hematopoietic stem cells) or can be terminally differentiated cells (e.g., muscle cells, neuronal cells, blood cells, connective tissue, or epithelial cells). As such, the method can be used to identify an agent that induces differentiation of stem cells in a SB cell population to terminally differentiated cells including pancreatic beta cells, hepatocytes, cardiomyocytes, skeletal muscle cells, or any other cell types. Agents or compound thus-identified can be used to treat degenerative disorders, cancer or immune disorders.

The expression level can be determined at either the mRNA level or the protein level. Methods of measuring mRNA levels in a sample are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a sample are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}$I, $^{131}$I, $^{35}$S, $^{3}$H, or $^{32}$P), enzymes (e.g., alkaline phosphatase, horseradish peroxidase, luciferase, or □-glactosidase), fluorescent/luminescent agents (e.g., fluorescein, rhodamine, phycoerythrin, GFP, BFP, and nanoparticles (e.g., Qdot™ supplied by the Quantum Dot Corporation, Palo Alto, Calif.). Other applicable methods include quantitative immunoprecipitation or complement fixation assays.

A test compound or agent can be any type of molecule, for example, a polynucleotide, a peptide, a peptidomimetic, peptoids such as vinylogous peptoids, a small organic molecule, or the like, and can act in any of various ways to alter a function of stem cells in a SB cell population. For example, the test agent can act extracellularly by binding to a cell surface receptor expressed by the cells, thereby altering a function mediated by binding of a ligand that generally binds to and acts via the receptor. Alternatively, the test agent can be one that traverses the cell membrane, either passively or via an active transport mechanism, and acts within the cells to alter a function.

A peptide test agent can be any polymer of amino acids or amino acid analogs, and can vary from about three to four residues to hundreds or thousands. Peptide test agents can be prepared by chemical synthesis, or using methods of protein purification, followed by proteolysis and, if desired, further purification by chromatographic or electrophoretic methods, or can be expressed from an encoding polynucleotide. A peptide test agent can be based on a known peptide, for example, a naturally occurring peptide, but can vary from the naturally occurring sequence, for example, by containing one or more amino acid analogs.

A polynucleotide agent can be a sequence of two or more deoxyribonucleotides or ribonucleotides that are linked together by a phosphodiester bond. It can be RNA or DNA, which can be a gene or a portion thereof, a cDNA, an RNAi agent, a synthetic polydeoxy-ribonucleic acid sequence, or the like, and can be single stranded or double stranded, as well as a DNA/RNA hybrid. It can be a naturally occurring nucleic acid molecule, which can be isolated from a cell, as well as a synthetic molecule, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond. Such nucleotide analogs are well known in the art and commercially available, as are polynucleotides containing such nucleotide analogs (Pagratis et al., Nature Biotechnol. 15:68-73, 1997).

A polynucleotide test agent can be contacted with or introduced into stem cells in a SB cell population using methods as disclosed herein or otherwise known in the art. Generally, but not necessarily, the polynucleotide is introduced into the cell, where it effects its function either directly, or following transcription or translation or both. For example, the polynucleotide can encode a peptide test agent, which is expressed in the cells and alters a function of the cells. A polynucleotide test agent also can be, or can encode, an antisense molecule, a ribozyme or a triplexing agent, which can be designed to target one or more specific target nucleic acid molecules.

Candidate agents or compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Lam, 1997, Anticancer Drug Des. 12:145. Examples of methods for the synthesis of molecular libraries can be found in, e.g., Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Felici 1991, J. Mol. Biol. 222:301-310; and U.S. Pat. No. 5,223,409).

Treating Degenerative Disorders

One can use stem cells in a SB cell population disclosed herein for treating degenerative or inherited diseases, avoiding ethical considerations of human embryo manipulation.

To do so, one can isolate a SB cell population from a patient, e.g., lacking a functional gene essential for proper development of a tissue or organ. One can then introduce into stem cells in the SB cell population an expression nucleic acid vector encoding a functional version of the gene. The vector can be introduced into the stem cells via a variety of techniques, including calcium phosphate co-precipitation, DEAE-dextran-mediated transfection, lipofection, electroporation, microinjection, or virus-meditated techniques. Methods not affecting the pluripotency of the cells are preferred. Description of such techniques can be found in, e.g., U.S. Pat. Nos. 7,422,736 and 5,591,625. After delivering the functional gene into the stem cells, one can transplant them back into the patient using method known in the art. As the stem cells are produced from the patient, the treatment does not cause immune rejection.

Alternatively, one can make universal donor cells from a SB cell population prepared from a healthy subject. The method for making universal donor cells are known in the art and that for making universal pluripotent stem cells from a SB cell population will be described below.

Under proper conditions, the transplanted stem cells can develop into a functional tissue or organ. To facilitate this development, the patient may be administered with factors to induce the development of the cells. Such factors can be small molecule compounds, peptides, and nucleic acids. Examples include, but are not limited to, transforming growth factor β, bone morphogenic proteins, and nerve growth factor.

The universal pluripotent stem cells are also useful for studying development or differentiation mechanisms of lineage development and differentiation. One can identify conditions for inducing the development of totipoent pluripotent stem cells into a specific tissue or organ using such cells as a model system. Further, one can isolate genes that play roles during the development using differential cDNA screening known in the art. One can prepare a cDNA library from the cells that have been induced to develop into a certain lineage, e.g., neuro-glial lineage described above. The library can then be used to isolate and study genes differentially expressed. These isolated genes can be further studied to define their roles in respective processes. The related techniques are known in the art. See e.g., U.S. Pat. No. 7,422,736. The pluripotent stem cells can also be used to develop into organs or clones of the animals using the methods known in the art. Accordingly, these cells are valuable for the pet and livestock industries, and can be used to preserve endangered animals.

In one aspect, the invention features a method of treating a degenerative disease in a subject. The method includes administering to a subject in need thereof an effective amount of the above-described stem cells. In one embodiment, at least one of these cells includes a recombinant nucleic acid. The recombinant nucleic acid can encode a polypeptide and the stem cell can contain an mRNA encoding the polypeptide. Examples of the degenerative disease include diabetes, a neurodegenerative disease, and arthritis. Examples of the neurodegenerative disease include Parkinson's disease.

In another aspect, the invention features a method of treating an autoimmune disease in a subject. The method includes administering to a subject in need thereof an effective amount of the above-described composition.

A subject to be treated for one of the above-described disorders can be identified by standard diagnosing techniques for that particular disorder. "Treating" refers to administration of a composition (e.g., a cell composition) to a subject, who is suffering from or is at risk for developing that disorder, with the purpose to cure, alleviate, relieve, remedy, delay the onset of, prevent, or ameliorate the disorder, the symptom of the disorder, the disease state secondary to the disorder, or the predisposition toward the damage/disorder. An "effective amount" refers to an amount of the composition that is capable of producing a medically desirable result in a treated subject. The treatment method can be performed alone or in conjunction with other drugs or therapies.

A degenerative disease refers to a disorder where the function or structure of an affected tissue or organ progressively deteriorate over time, whether due to genetic defects, injury, lack of proper cell differentiation (e.g., that in cell proliferative disorders), normal bodily wear, or lifestyle choices. Examples of degenerative diseases include neurodegenerative diseases (e.g., Alzheimer's disease, Parkinson disease, Huntington's disease, multiple sclerosis, and amyotrophic lateral sclerosis (ALS)); other nervous system disorders (e.g., transverse myelitis, demyelination occurring after trauma to the brain or spinal cord, acute brain injury, head trauma, spinal cord injury, peripheral nerve injury, ischaemic brain injury, hereditary myelin disorder of the CNS, epilepsy, perinatal asphyxia, asphyxia, anoxia, status epilepticus, Shy-Drager syndrome, autism, and stroke); cancer or a condition resulting from related cancers therapy (e.g., chemotherapy); metabolic disorders (e.g., diabetes/diabetes mellitus and Niemann Pick disease); autoimmune or inflammation related disorders (e.g., erythematosis, inflammatory bowel disease (IBD), postatitis, osteoarthritis, osteoporosis, rheumatoid arthritis, lupus, diabetes, and asthma); ocular disorders (e.g., glaucoma, retinitis pigmentosa, Norrie disease, and macular degeneration); heart and circulatory disorders (e.g., atherosclerosis, heart failure myocardial infarction, and cardiovascular disease); blood disorders (e.g., Wiscott Aldrich syndrome); muscular dystrophy; gastrointestinal disease; kidney disease; liver disease; lung disease; adrenal disorders (e.g., Addison's disease); a condition resulting from an injury (e.g., a burn, a stroke, damaged tissue, including flesh wounds, age damaged cells, and age damaged tissue); a condition associated with aging (e.g., hair loss, including male pattern baldness and alopecia areata); viral conditions (e.g., hepatitis C infection and acquired immune deficiency disorder); and any other disorder that an organ transplant or stem cells can be used to restore, regenerate, or otherwise ameliorate signs and/or symptoms associated with the disorder. The method of this invention can be used in treating erectile dysfunction and in plastic surgery or breast implantation for female.

Within the scope of this invention is a method of treating brain or CNS tissue damage or alleviate the symptom of the disorder in a subject. The method includes identifying a subject suffering from or being at risk for developing brain tissue damage. The subject can be a human or a non-human mammal, such as a cat, a dog, or a horse. Examples of the brain tissue damage include those caused by a cerebral ischemia (e.g., chronic stroke) or a neurodegenerative disease (e.g., Parkinson's disease, Alzheimer's disease, Spinocerebellar disease, and Huntington's disease). A subject to be treated can be identified by standard techniques for diagnosing the conditions or disorders of interest. The treatment method entails administering to a subject in need thereof an effective amount of the above-described stem cells or active agents/compounds.

The therapeutic effects of the stem cells can be accessed according to standard methods. For example, to confirm efficacy in promoting cerebrovascular angiogenesis, one can examine the subject before and after the treatment by standard brain imaging techniques, such as computed tomography (CT), Doppler ultrasound imaging (DUI), magnetic resonance imaging (MRI), and proton magnetic resonance spectroscopy ($^1$H-MRS). For example, $^1$H-MRS represents a non-invasive means to obtain biochemical information correlated to brain metabolic activity (Lu et al., 1997, Magn. Reson. Med. 37, 18-23). This technique can be applied to evaluate the metabolic changes involved in cerebral ischemia with or without stem cell transplantation. For example, it can be used to study the N-acetylaspartate (NAA) concentration in the brain, a marker of neuronal integrity. Although NAA redistribution and trapping in neuronal debris limits its use as a quantitative neuronal marker, decreases in brain NAA concentration in cerebral ischemia can be considered as an index of neuronal loss or dysfunction (Demougeot et al., 2004, J. Neurochem. 90, 776-83). Therefore, an NAA level, measured by $^1$H-MRS, is a useful indicator for following the effect of stem cell transplantation after cerebral ischemia.

Gene Therapy

The stem cells described herein can be used to express exogenous, recombinant polypeptide. Thus, within the scope of this invention are such stem cells, which contain a recombinant nucleic acid. The recombinant nucleic acid can encode a polypeptide and the stem cells can contain an mRNA encoding the polypeptide.

These stem cells can be genetically manipulated so that they do not express the beta2-microglobulin gene or do not express one or more proteins encoded by the class I major histocompatibility complex (MHC) genes that elicit a T lymphocyte mediated reaction against the cell. These cells can be used as universal donor cells since they do not lead to host rejections of grafts.

Accordingly, the invention features a method for introducing a heterologous nucleic acid in a subject. The method includes the steps of obtaining the above-described stem cells, where at least one of the stem cells includes a heterologous nucleic acid, and administering the cell into a subject in need thereof. The heterologous nucleic acid can encode a polypeptide.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell. Similarly, a heterologous protein indicates that the protein comprises two or more subsequences that are not found in the same relationship to each other in nature (e.g., a "fusion protein," where the two subsequences are encoded by a single nucleic acid sequence). Such protein can be generated by recombinant techniques.

The term "recombinant" when used with reference, e.g., to a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

The above-described stem cells and methods can be used in various gene therapy methods known in the art. Gene therapy includes both ex vivo and in vivo techniques. Specifically, the above-described stem cells can be genetically engineered ex vivo with an oligonucleotide modulator or a nucleic acid molecule encoding the modulator, with the engineered cells then being provided to a patient to be treated. Cell cultures may be formulated for administration to a patient, for example, by dissociating the cells (e.g., by mechanical dissociation) and intimately admixing the cell with a pharmaceutically acceptable carrier (e.g., phosphate buffered saline solution). Alternatively, cells may be cultured on a suitable biocompatible support and transplanted into a patient. The engineered cells are typically autologous so as to circumvent xenogeneic or allotypic rejection. Such ex vivo methods are well known in the art.

The cells can be engineered by administration of the oligonucleotide or nucleic acid molecule using techniques known in the art. For example, oligonucleotides and other nucleic acid molecules can be administered by direct injection of a "naked" nucleic acid molecule (U.S. Pat. No. 5,679, 647) or a nucleic acid molecule formulated in a composition with one or more other agents which facilitate uptake of the nucleic acid molecule by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the nucleic acid molecule with lipids, cell-surface receptors or transfecting agents; by encapsulation of the nucleic acid molecule in liposomes, microparticles, or microcapsules; by administration of the nucleic acid molecule linked to a peptide which is known to enter the nucleus; or by administration of the nucleic acid molecule linked to a ligand subject to receptor-mediated endocytosis, which can be used to target cell types specifically expressing the receptors.

A nucleic acid-ligand complex can be formed in which the ligand comprises a fusogenic viral peptide to disrupt endosomes, allowing the nucleic acid to avoid lysosomal degradation; or the nucleic acid molecule can be targeted for cell specific uptake and expression in vivo by targeting a specific receptor. In addition, an efficient method for the introduction, expression and accumulation of antisense oligonucleotides in the cell nucleus is described in U.S. Pat. No. 6,265,167, which allows the antisense oligonucleotide to hybridise to the sense mRNA in the nucleus, and thereby prevents the antisense oligonucleotide being either processed or transported into the cytoplasm. The present invention also contemplates the intracellular introduction of the nucleic acid molecule and subsequent incorporation within host cell DNA for expression by homologous recombination known in the art.

The polynucleotide can also be incorporated into a suitable expression vector. A number of vectors suitable for gene therapy applications are known in the art (see, for example, Viral Vectors: Basic Science and Gene Therapy, Eaton Publishing Co. (2000)).

The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise. A variety of plasmids are now readily available commercially and include those derived from *Escherichia coli* and *Bacillus subtilis*, with many being designed particularly for use in mammalian systems. Examples of plasmids that may be used in the present invention include, but are not limited to, the eukaryotic expression vectors pRc/CMV (Invitrogen), pCR2.1 (Invitrogen), pAd/CMV and pAd/TR5/GFPq (Massie et al., (1998) Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or PVAX Invitrogen).

The expression vector can be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous oligonucleotides or genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leukemia Virus, spleen necrosis virus, Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumour virus. Specific retroviruses include pLJ, pZIP, pWE and pEM, which are well known to those skilled in the art.

Cell Banking

The invention features a stem cell bank or library for a convenient systematic access to different stem cell lines. A SB cell population in the bank or library is derived from a healthy subject or subject having known disease state or disease symptom would be invaluable to users, e.g., researchers. Also with the scope of the invention is a cell bank or library having cells differentiated from the above-described stem cells. Examples of cells differentiated from the stem cells include brain cells, neurons, astrocytes, glial cells, T cells, B cells, cartilage cells, bone cells, pancreatic islet cells, fat cells, heart cells, liver cells, kidney cells, lung cells, muscle cells, and eye cells. The subjects may be human or nonhuman vertebrates. The stem cells can be derived from any mammalian organism, such as human, mouse, rabbits, cows, pigs, and the like.

The cells in the bank or library are catalogued according to predetermined characteristics, including phenotypic information, morphological characteristics, differentiation profile, blood type, major histocompatibility complex, disease state of donor, or genotypic information (e.g. single nucleated polymorphisms (SNPs) of a specific nucleic acid sequence associated with a gene, or genomic or mitochondrial DNA). The cells are stored under appropriate conditions (typically by freezing) to keep the stem cells alive and functioning. Cataloguing may constitute creating a centralized record of the characteristics obtained for each cell population, such as, but not limited to, an assembled written record or a computer database with information inputted therein. Essentially, this embodiment pertains to the production of a stem cell bank. The stem cell bank facilitates the selection from a plurality of samples of a specific stem cell sample suitable for a user's needs. Thus, another embodiment of the subject invention pertains to a stem cell bank comprising a plurality of stem cells samples obtained from separate sources and which are characterized and catalogued according to at least one predetermined characteristic. An additional embodiment pertains to a method of establishing a stem cell bank comprising collecting stem samples from multiple sources; cataloguing the samples according to at least one predetermined characteristic and storing the cells under conditions that keep cells viable.

With the scope of this invention is a stem cell banking system containing a plurality of stem cell populations disposed in individual containers under conditions to keep the stem cell populations viable; a database computer comprising at least one processing module, a display, and a storage medium comprising information of at least one characteristic for each stem cell population; and at least one program code module for causing the information to be viewable on said display upon command by a user. In a specific embodiment, the invention features a stem cell banking system where stem cell populations have stem cells obtained from subjects who have a disease condition. The disease condition may include the above-described degenerative diseases. SB cell populations are harvested from different subjects having different diseases, and the stem cells are characterized. The characteristic(s) is/are inputed into the database computer. In addition, or alternatively, cells are characterized based on a specific phenotype not necessarily associated with a disease condition. For example, liver cells can be characterized based on their ability to metabolize certain compounds such as caffeine, alcohol, drug agents, etc. to study genetic bases of such different metabolism abilities, or underlying physiology associated therewith. Other types of cells can be characterized based on functional and/or morphological phenotypes.

In certain embodiments, cells differentiated from stem cells in an SB cell population may be subjected to conditions to influence differentiation or dedifferentiation through introduction of engineered vectors, or other genetic material. Dedifferentiation comprises the manipulation of a cell such that it takes on the properties of a less differentiated cell.

The stem cell libraries of the invention can be used to screen for agents or compounds that may be used to treat degenerative disorders, cancer or immune disorders in the manner described above. The libraries are suitable for high throughput screening and are useful for identifying agents that are specifically effective for a particular subject. For a high throughput screening, stem cells can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the cells, particularly with respect to the function being examined. An advantage of using a high throughput format is that a number of test agents can be examined in parallel, and, if desired, control reactions also can be run under identical conditions as the test conditions. As such, the screening methods of the invention provide a means to screen one, a few, or a large number of test agents in order to identify an agent that can alter a function of stem cells, for example, an agent that induces the cells to differentiate into a desired cell type, or that prevents spontaneous differentiation, for example, by maintaining a high level of expression of regulatory molecules.

Universal Donor Cells

The above-described stem cells can be genetically engineered to generate histocompatible donor cells or tissues for transplantation. The goal of transplantation and cell therapy is to successfully replace failing tissues or organs with functional donor tissues or organs. However, for transplantation to succeed, two major barriers need to be overcome: the availability of suitable donor tissues or organs and immune rejection. The replacement of failing tissues or organs and the treatment of the rejection is restricted by the limited number of acceptable donors and the need for co-administration of toxic immuno-suppressive drugs in conjunction with long term immuno-suppressive protocols. Current and experimental transplantation protocols rely mainly on sibling donors, other small pools of allogeneic donors, and xenogeneic donors. The above-described genetically engineered stem cells can be used to overcome these limitations.

More specifically, the stem cells described herein can be genetically engineered to not express on their surface class II MHC molecules. More preferably, the cells are engineered to not express substantially all cell surface class I and class II MHC molecules. As used herein, the term "not express" mean either that an insufficient amount is expressed on the surface of the cell to elicit a response or that the protein that is expressed is deficient and therefore does not elicit a response.

The MHC molecules refer to HLA molecules, specifically of classes HLA A, B and C, and class II HLA DP, DQ, and DR, and their subclasses. This terminology is generally construed as specific to the human MHC, but is intended herein to include the equivalent MHC genes from the donor cell species, for example, if the cells are of porcine origin, the term HLA would refer to the equivalent porcine MHC molecules, whether MHC I or II. When the class II MHC molecules are removed, CD4+ T-cells do not recognize the genetically engineered endothelial cells; when both the class I and class II MHC molecules are removed neither CD4+ nor CD8+ cells recognize the modified cells.

The preferred genetic modification performed on the stem cells includes 1) disrupting the endogenous invariant chain gene which functions in the assembly and transport of class II MHC molecules to the cell surface and loading of antigenic peptide, and 2) disrupting the endogenous $\beta_2$-microglobulin gene ($\beta_2$M gene), which codes for a protein required for the cell surface expression of all class I MHC molecules. Alternatively, just the invariant chain gene is disrupted. Invariant chain is believed to be required for the insertion of antigenic peptide fragments into the MHC class II molecule. Together, the antigenic peptide and MHC are recognized by T cells. In the absence of antigenic peptide, T cell recognition is not normally obtained, nor is the MHC class II molecule folded properly. Thus, in cells lacking invariant chain, presentation of peptide will be abrogated and even if minuscule amounts of cell surface MHC are obtained, they may be devoid of peptide and therefore, non-immunogenic.

Disruption of these genes can be accomplished by means of homologous recombination gene targeting techniques. These techniques are well known in the art. See e.g., U.S. Pat. Nos. 6,916,654 and 6,986,887.

Compositions

The present invention provides for pharmaceutical compositions containing the above-described cells or active agents/compounds. Pharmaceutical compositions can be prepared by mixing a therapeutically effective amount of the cells or active agents/compounds, and, optionally other active substance, with a pharmaceutically acceptable carrier. The carrier can have different forms, depending on the route of administration. Examples of other active substance include active compounds known or identified by the screening method of described above.

The above-described pharmaceutical compositions can be prepared by using conventional pharmaceutical excipients and methods of preparation. All excipients may be mixed with disintegrating agents, solvents, granulating agents, moisturizers, and binders. As used herein, the term "effective amount" or 'therapeutically effective amount' refers to an amount which results in measurable amelioration of at least one symptom or parameter of a specific disorder. A therapeutically effective amount of the above-described stem cells can be determined by methods known in the art. An effective amount for treating a disorder can easily be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeia for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions described above refers to a diluent, excipient, or vehicle with which a compound is administered. Such pharmaceutical carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The above-described stem cells can be administered to individuals through infusion or injection (for example, intravenous, intrathecal, intramuscular, intraluminal, intratracheal, intraperitoneal, or subcutaneous), orally, transdermally, or other methods known in the art. Administration may be once every two weeks, once a week, or more often, but frequency may be decreased during a maintenance phase of the disease or disorder.

Both heterologous and autologous cells can be used. In the former case, HLA-matching should be conducted to avoid or minimize host reactions. In the latter case, autologous cells are enriched and purified from a subject and stored for later use. The cells may be cultured in the presence of host or graft T cells ex vivo and re-introduced into the host. This may have the advantage of the host recognizing the cells as self and better providing reduction in T cell activity.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art. In all of the above-described methods, the stem cells can be administered to a subject at $1\times10^4$ to $1\times10^{10}$/time.

Evaluation Method

The stem cells and methods disclosed herein can be used to evaluate a subject. Generally, a young healthy subject has a relative higher percentage of stem cells (such as SSEA4+ cells, CD66e+/BLSCs, or CD9+/SB-1 cells). As discussed in Example 4 below, the numbers or parentages of these cells decrease as the subject ages or due to genetic defect or expose to unfavorable environmental factors. This decrease compromises the subject's stem-cell related abilities, including ability to repair tissue after an injury.

Also as shown in Example 4 below, these changes can be used to evaluate a subject risk for having an ageing related disorder. For example, if a subject has higher-than-average level, he or she has excellent ability to repair tissue after an injury and high risk of develop cancer. In other words, a high level of the above-mentioned stem cells in a sample from the subject indicates that a subject has a young development status with (1) a better ability to repair tissue damage, to recover from an injury, and to defend pathogens and (2) lower probabilities of developing an autoimmune disease, a cardiovascular disease, diabetes, and other disorders associated with ageing. On the other hand, such a higher level is positively correlated with a higher risk of having cancer.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE 1

A blood sample or a bone marrow sample was drawn from a person and placed in an anti-clotting EDTA tube or heparin tube. After sitting the tube for 6 to 48 hours in 4° C., the sample separated into two layers. The top layer contained a SB cell population, which were further analyzed by C6 accuri flow cytometry, immunocytochemistry, and RNA extraction/RT-PCR. The bottom layer contained red and white blood cells, which are not smaller than 6.0 µm.

Particles in the top layer were analyzed by the size beads of flow cytometry. It was found that they were less than 6.0 µm. It is known that platelets and microparticles are smaller than 6.0 µm, but have no nuclei and therefore cannot be stained by DAPI or SYTO. To examine the particles, DAPI and SYTO staining were carried out. The results showed that many particles were stained positive by both dyes, i.e., DAPI and SYTO, suggesting that these particles were cells containing DNA nuclei, but not platelets and microparticles. It was further found that the DAPI-negative particles were about 0.01 to 1.5 µm. These results suggest that the top layer (named as StemBios cell population or SB cell population) contained cells/stem cells, platelets and microparticles.

To confirm that the DAPI-positive particles were indeed cells, those particles were plated in cell culture dishes and cultured in an Opti-MEM medium containing 3% FBS and 10 nM of bFGF and EGF.

After being cultured for one week, the dishes were examined under a microscope. It was found that number of the particles increased and that a number of cells of sizes larger than 3 µm appeared. DAPI staining again demonstrates DNA in the particles. After a few weeks of culture, some of the cells formed spheres. In addition, some of the cells exhibited GAPDH gene expression as demonstrated by RT-PCR, using primers:

```
                                         (SEQ ID NO: 1)
AGC TGA ACG GGA AGC TCA CT
and
                                         (SEQ ID NO: 2)
TGC TGT AGC CAA ATT CGT TG.
```

To further confirm that the DAPI positive particles were cells, the particles were incubated and infected with Lenti viruses that contained a GFP expression cassette using a standard technique. After the incubation, the particles were found to express GFP. As the Lenti virus must integrate to chromosome so as to express the GFP, the results suggest that the particles contained chromosomes.

These results proved that those particles that were less than 3 µm are indeed cells, which could proliferate and give rise to cells of sizes larger than 3 µm.

Figure 2:
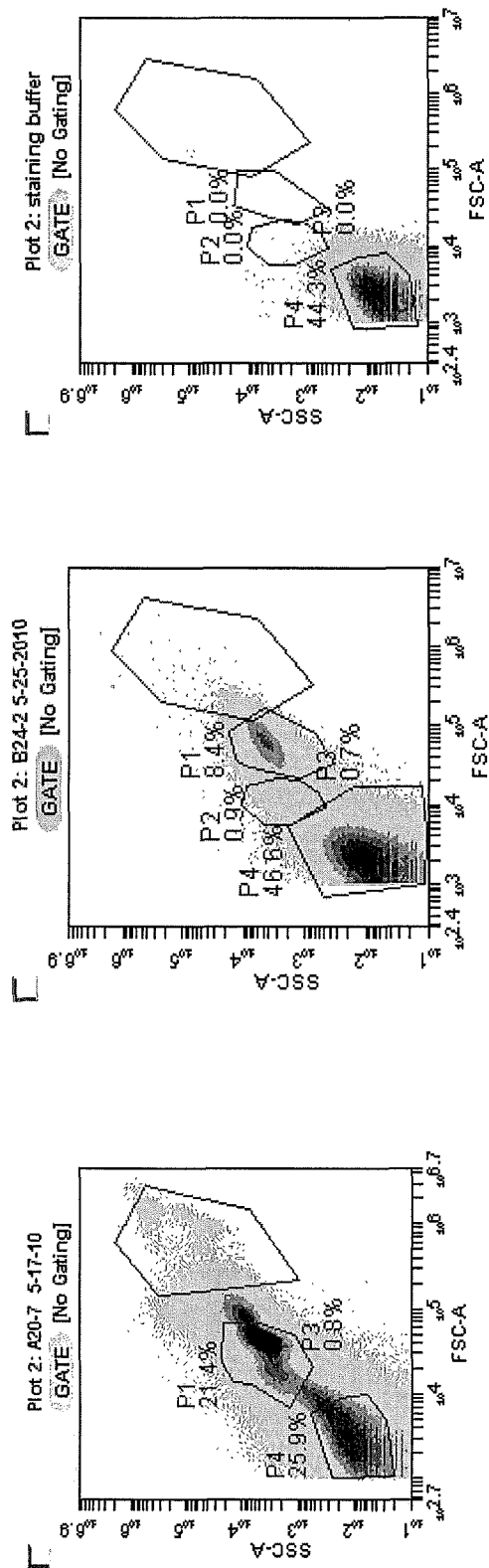
FIG. 2 includes three scatter plots showing cells in the P3-gated region each having a size less than 6 microns as analyzed by flow cytometry. The left panel is a plot showing whole blood having both large (>6 microns) and small cells; the middle panel is a plot showing cells in a SB cell population after purification; and the right panel is a plot showing buffer only.

The cells were then subjected to C6 accuri flow cytometry to ascertain their sizes. Specifically, beads with sizes from 0.1 to 7 µm were conjugated with FITC and analyzed by the flow cytometry. Based on the scattering patterns of these beads shown in FIG. 1, the sizes of the cells in the P3 gated region shown in FIG. 2 were determined to be 0.3 to 6 µm. In contrast, red blood cells (RBC) each had a size of about 6 µm and T lymphocytes each had a size of about 6 to 7 µm. Further analyses with DAPI indicate that 90% of the particles in the P3-gated region were living cells as they exhibit nucleus staining.

Figure 3:
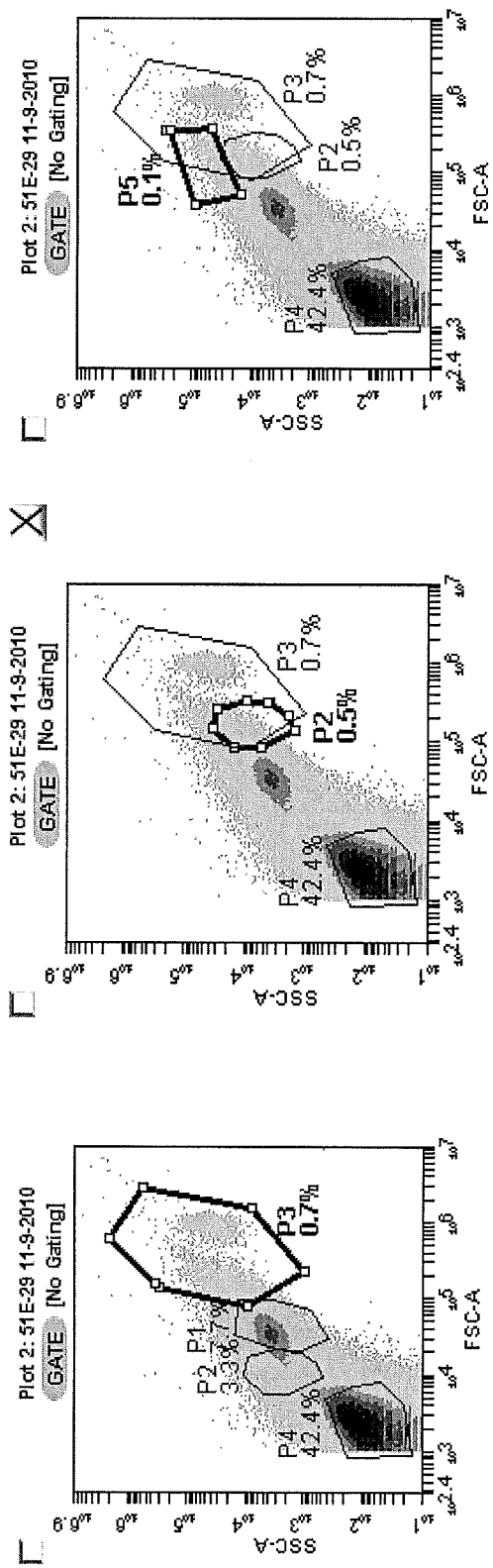
FIG. 3 includes three scatter plots showing that a SB cell population in the P3 gated region included SB-1 cells in the P2 gated region and SB-2 cells in the P5-gated region. Note that buffer, platelets, and microparticles were shown in the P4, P1, and P2-gated regions, respectively.
Figure 4:
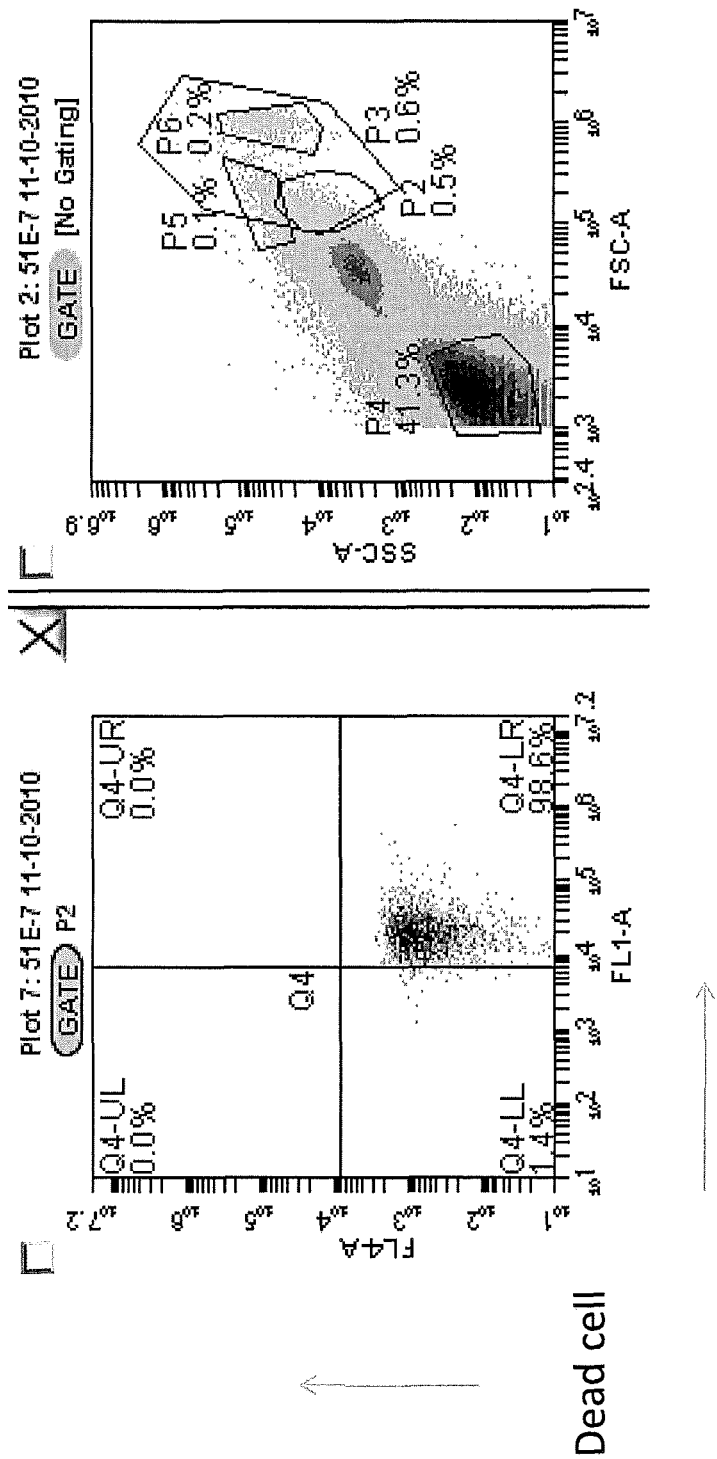
FIG. 4 includes two scatter plots showing SB-1 cells in the P2-gated region, which were isolated from blood. As shown in the left panel, almost all of the SB-1 cells were stained positive by SYTO.
Figure 5:
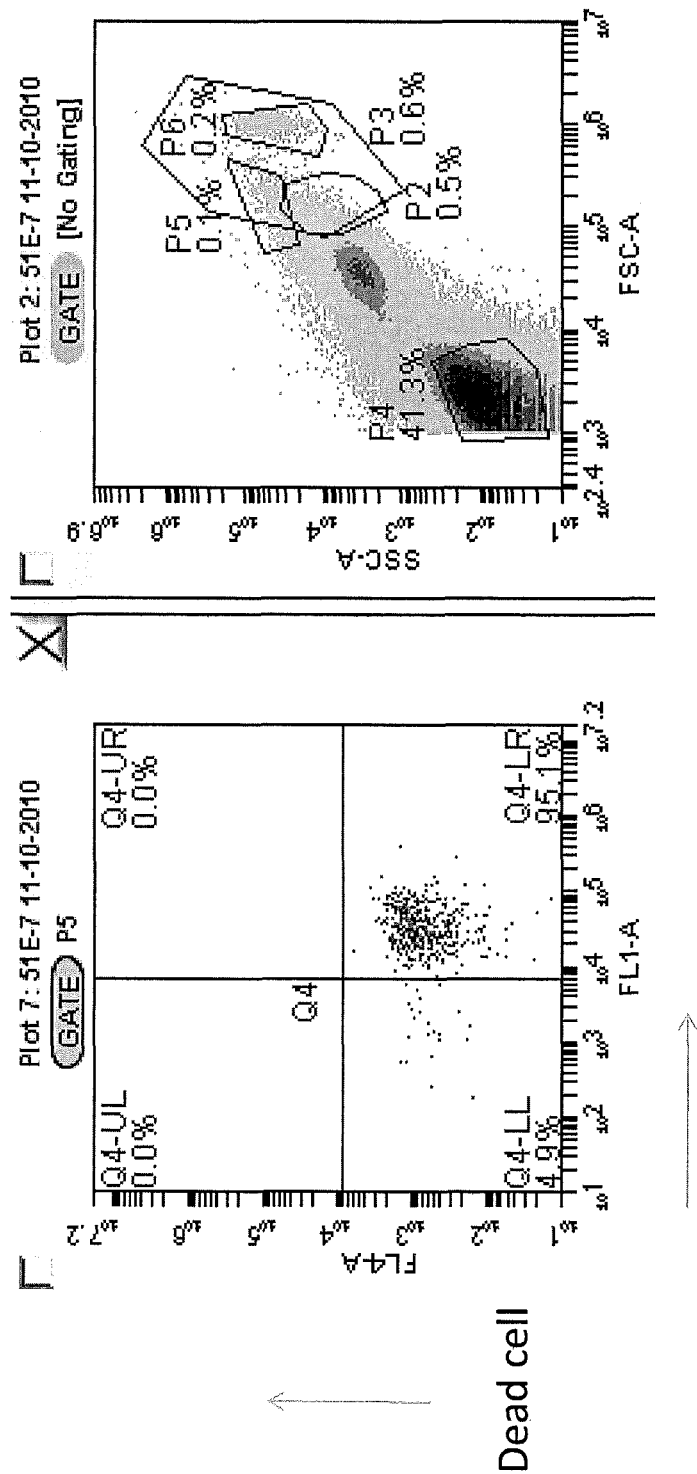
FIG. 5 includes two scatter plots showing SB-2 cells in the P5-gated region, which were isolated from blood. As shown in the left panel, almost all of the SB-2 cells were stained positive by SYTO.
Figure 6:
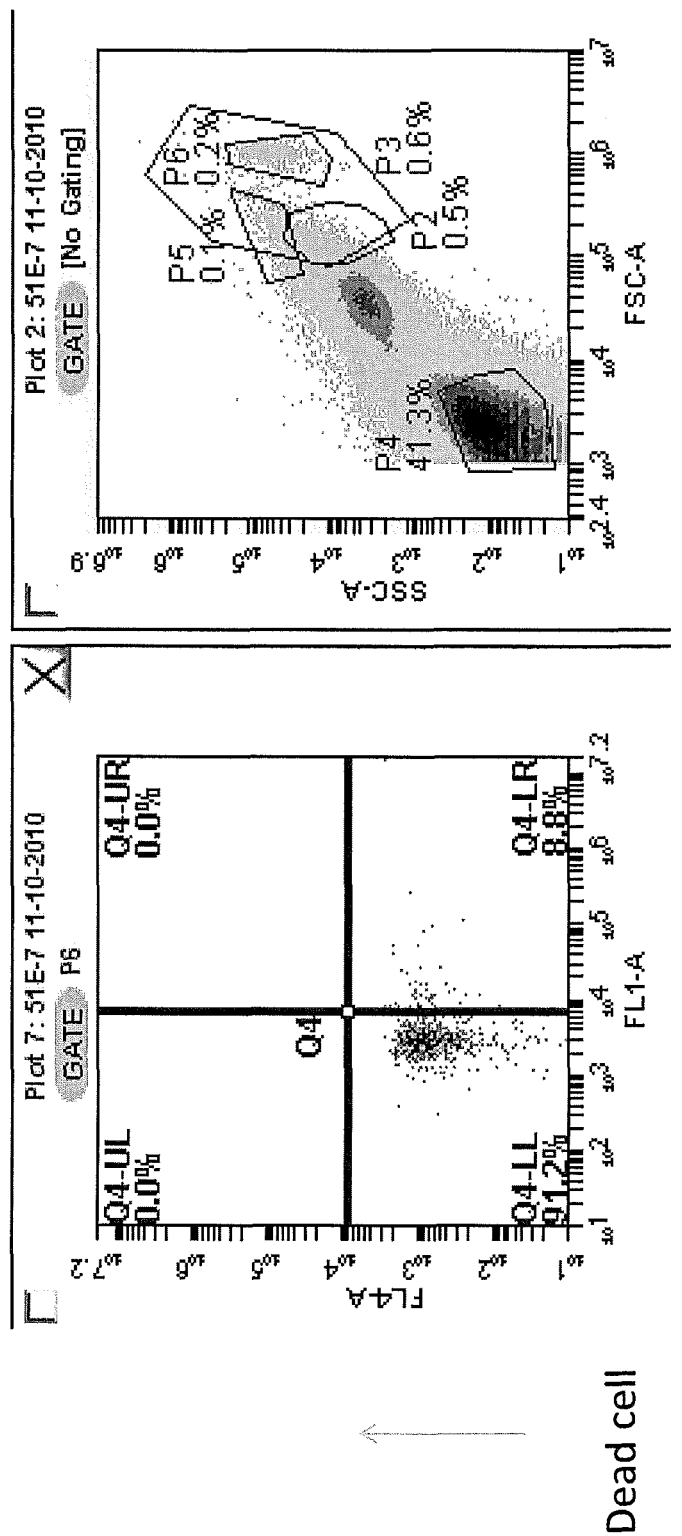
FIG. 6 includes two scatter plots showing red blood cells in the P6-gated region, which were isolated from blood. As shown in the left panel, all of the red blood cells were stained negative by SYTO.

All cells in a SB cell population prepared using an EDTA tube were then subjected to cell marker analysis. It was found that over 70% of the cells in the P3-gated region of an isolated SB cell population (FIG. 3) stained strongly positive for CD9 and 98% of them were also stained positive by SYTO (FIG. 4). In some cases, as much as 90% of the cells in the P3-gated region of the SB cell population were CD9+. These CD9+ cells that were stained positive by SYTO are named "SB-1 cells." It was also found that about 15% of the cells in the P3 gated region of a SB cell population (FIG. 3) were stained positive for SSEA1+, SSEA4+, CD13+, and/or Stro1+. Almost all of these cells were also stained positive by SYTO (FIG. 5). They are named "SB-2 cells." In contrast, CD235a+ RBCs in the P6-gated region were stained negative by SYTO (FIG. 6).

Further, it was found that all SB cell populations tested contained CD349+ cells. Among the CD9+ cells, as high as about 25% of them were also CD349+. RT-PCR analyses show that stem cells in the SB cell population expressed CD9, CD349, Oct4, and Nanog, but not Sox2 and CXCR4. The primers for RT-PCR are shown below:

```
GAPDH
                                         (SEQ ID NO: 1)
F: 5'-AGC TGA ACG GGA AGC TCA CT-3'

(SEQ ID NO: 2)
R: 5'-TGC TGT AGC CAA ATT CGT TG-3'

4-Oct
                                         (SEQ ID NO: 3)
F: 5'-CTC ACC CTG GGG GTT CTA TT-3'

(SEQ ID NO: 4)
R: 5'-CTC CAG GTT GCC TCT CAC TC-3'

Nanog
                                         (SEQ ID NO: 5)
F: 5'-CAT GAG TGT GGA TCC AGC TTG-3'

(SEQ ID NO: 6)
R: 5'-CCT GAA TAA GCA GAT CCA TGG-3'

Sox 2
                                         (SEQ ID NO: 7)
F: 5'-TCG GCG CCG GGG AGA TAC AT-3'

(SEQ ID NO: 8)
R: 5'-CCC CCG GCG GCA ATA GCA-3'

CD9
                                         (SEQ ID NO: 9)
F: 5'-TGCACCAGACCAGTGCAAACATTC-3'

(SEQ ID NO: 10)
R: 5'-ACTTGGCTGCTGTCACTTTCATGC-3'

CD349
                                         (SEQ ID NO: 11)
F: 5-TGATGAGCTGACTGGGCTTTGCTA-3'

(SEQ ID NO: 12)
R: 5'-TGACCATGAGCTTCTCCAGCTTCT-3'
```

CXCR4

(SEQ ID NO: 13)
F: 5'-CCA TTG TCC ACG CCA CCA AC-3'

(SEQ ID NO: 14)
R: 5'-TGA GTG CAT GCT GGG CAG AG-3'

Additional analyses of 40 different blood samples by flow cytometry show that the above-mentioned P3 gated region of the SB cell population contained less than 5% of the cells that are CD31+, CXCR4+, CD66+ and/or CD271+. In most of the samples, this region contained less than 1% of the cells that are CD66e or CD66a positive, while only three samples had more than 2% of the cells that are CD66e or CD66a positive. This suggested that the Blastomere-like stem cells are not a major component of a SB stem cell population. Indeed, it was found that CD9+ or CD9+CD349+ cells are a major component in a SB stem cell population.

Further, it was found that some cells in a SB cell population were positive for CD90, a marker for mesenchymal stem cells (MSCs); and some were positive for CD34, a maker for hematopoietic stem cells (HSCs). Yet, these cells accounted for less than 1% of the cells in the above-mentioned P3-gated region of the SB cell population. In addition, less than 1% of the cells in the above-mentioned P3-gated region of the SB cell population were stained positive for CD133.

Even though a SB cell population may contain the platelets, however, the half life of platelets is only 5-9 days. The SB cell population can survive in the 4° C. for more than 12 days after withdrawn the blood in EDTA or heparin tube and still has very strong CD9 and CD349 expression.

Interestingly, in one assay, a SB cell population was prepared from an 18 year-old patient who had an immune disease. After this sample was examined for the above-mentioned stem cell markers, it was found that this patient had a higher level of SSEA4, CD66e, CXCR4, SSEA1, Stro1, CD34, CD9, CD349, CD56, or CD184 as compared that of other healthy people (control level).

EXAMPLE 2

Assays were carried out to demonstrate that SB cells, which, as pointed out above, proliferate, are stem cells capable of differentiating into different cells lineages.

Briefly, a SB cell population was obtained from a subject in the manner described above. The cells were then cultured in a differentiation medium. After two weeks, it was found that, in the culture, CD9+CD349+ and CD9+CD349– cells formed spheres and the cells of the spheres were positive for SSEA4 (an ES cell marker), CD66e (a BLSC marker), CD90, and CD73. It was also found that stem cells in a SB cell population formed zygote-like structures and grew into multiple-layers on a collagen-coated plate.

Additional assays were carried out to examine the ability of a SB cell population to further differentiate into ectoderm (e.g., neural cells and epidermal cells), mesoderm (e.g., adipocytes, osteogenic cells, and muscle cells), and endoderm cells (e.g., hepatocyte and islet cells). All primers used for detecting differentiation markers with real time RT-PCR are listed below:

GADPH (SEQ ID NO: 15)
F: 5'-GAGTCAACGGATTTGGTCGT-3'

(SEQ ID NO: 16)
R: 5'-TTGATTTTGGAGGGATCTCG-3'

GABAR (SEQ ID NO: 17)
F: 5'-TTATCTCACCCCTTCCTTGG-3'

(SEQ ID NO: 18)
R: 5'-GCCATCATGTAGCATTCCTG-3'

HNF4a (SEQ ID NO: 19)
F: 5'-TGTGAGTGGCCCCGACCCTG-3'

(SEQ ID NO: 20)
R: 5'-ACGATTGTGGCGACGGCTCC-3'

CD44

(SEQ ID NO: 21)
F: 5'-TCGAAGAAGGTGTGGGCAGAAGA-3'

(SEQ ID NO: 22)
R: 5'-ATTTCCTGAGACTTGCTGGCCTCT-3'

Albumin (SEQ ID NO: 23)
F: 5'-TGTGAAACACAAGCCCAAGGCA-3'

(SEQ ID NO: 24)
R: 5'-CCCTCCTCGGCAAAGCAGGT-3'

CD10

(SEQ ID NO: 25)
F: 5'-GGTTGGGAGCTGATGAAACT-3'

(SEQ ID NO: 26)
R: 5'-GAATAGGGCTGGAACAAGGA-3'

CD31

(SEQ ID NO: 27)
F: 5'-CAGGCTTCGGCTCAGGCACC-3'

(SEQ ID NO: 28)
R: 5'-ATCGGGGCCGGGTGACTTCA-3'

CD133

(SEQ ID NO: 29)
F: 5'-AGCGATCAAGGAGACCAAAG-3'

(SEQ ID NO: 30)
R: 5'-AAGCACAGAGGGTCATTGAG-3'

CXCR4

(SEQ ID NO: 31)
F: 5'-GTTGGCTGAAAAGGTGGTCT-3'

(SEQ ID NO: 32)
R: 5'CACAACCACCCACAAGTCAT-3'

NR4A2

(SEQ ID NO: 33)
F: 5'-GCTCAAGGAACCCAAGAGAG-3'

(SEQ ID NO: 34)
R: 5'-GGCACCAAGTCTTCCAATTT-3'

MAP-2

(SEQ ID NO: 35)
F: 5'-CGCACACCAGGCACTCCTGG-3'

(SEQ ID NO: 36)
R: 5'-CACCTGGCCTGTGGCGGATG-3'

```
Nestin
                                         (SEQ ID NO: 37)
F: 5'-TGCCCGGCACTGGGGACTTA-3'

(SEQ ID NO: 38)
R: 5'-TAGCGGGCCAGGCCTCTCAG-3'

N-Cam
                                         (SEQ ID NO: 39)
F: 5'-CTCCAGCACAGCCCAGGTGC-3'

(SEQ ID NO: 40)
R: 5'-TGCTGGCTTCCTTGGCATCATGC-3'

Tau
                                         (SEQ ID NO: 41)
F: 5'-AAGATCGGCTCCACTGAGAA-3'

(SEQ ID NO: 42)
R: 5'-GGACGTGGGTGATATTGTCC-3'

Insulin
                                         (SEQ ID NO: 43)
F: 5'-AGCCTTTGTGAACCAACACC-3'

(SEQ ID NO: 44)
R: 5'-GCTGGTAGAGGGAGCAGATG-3'

Transferrin
                                         (SEQ ID NO: 45)
F: 5'-GAGGCCACTAAGTGCCAGAG-3'

(SEQ ID NO: 46)
R: 5'-TTCTTCACCACAGCAACAGC-3' a-feto protein
                                         (SEQ ID NO: 47)
F: 5'-AAATGCGTTTCTCGTTGCTT-3'

(SEQ ID NO: 48)
R: 5'-GCCACAGGCCAATAGTTTGT-3'

CD105
                                         (SEQ ID NO: 49)
F: 5'-CACTAGCCAGGTCTCGAAGG-3'

(SEQ ID NO: 50)
R: 5'-CTGAGGACCAGAAGCACCTC-3'

Tyrosine Hydroxylase
                                         (SEQ ID NO: 51)
F: 5'-GCTCAGGAGCTATGCCTCAC-3'

(SEQ ID NO: 52)
R: 5'-ACCTAGCCAATGGCACTCAG-3'

Neurofilament-M
                                         (SEQ ID NO: 53)
F: 5'-AAGTCAGACCAAGCCGAAGA-3'

(SEQ ID NO: 54)
R: 5'-GCACAGGAGACTTGCCTTTC-3'

Myosin heavy chain alpha 6
(cardiomyocyte)
                                         (SEQ ID NO: 55)
F: 5'-GCTGGAGTCCTCACAGAAGG-3'

(SEQ ID NO: 56)
R: 5'TCTCCAGCTCATGCACATTC-3'

Myosin light chain 1 fast
(skeletal myocyte)
                                         (SEQ ID NO: 57)
F: 5'-TTCAGTGCTGACCAGATTGC-3'

(SEQ ID NO: 58)
R: 5'-AAATGGCTTGCATCATAGGC-3'

Osteocalcin (OC)
                                         (SEQ ID NO: 59)
F: 5'-TGAGAGCCCTCACACTCCTC-3'

(SEQ ID NO: 60)
R: 5'-TCAGCCAACTCGTCACAGTC-3'
```

A SB cell population from bone marrow was induced to express nestin, an early marker for formation of neuron (ectoderm) and islet cells (endoderm). Briefly, a SB cell population was cultured in a standard medium for two to four weeks and then switched into an induction medium that contains 10 nM glucocorticoid and 10% FBS. After 1-month treatment, RNA was extracted and gene expression was determined by Real Time PCR. Expression of nestin was detected by RT-PCR with a primer pair: SEQ ID NOs: 37 and 38.

Endoderm cells are characterized by their polygonal shapes. Expression of two hepatocyte markers (transferrin and albumin) and three islet cell markers (insulin, alpha-Fetoprotein, and HNF4 alpha) were detected. In addition, both Western blot and ELISA also detected expression of albumin in differentiated cells. These results indicate that stem cells in a SB cell population were differentiated into hepatocytes and some were differentiated into islet cells.

Ectoderm cells are characterized by their filament-like feature. Differentiation of stem cells in a SB cell population to neuronal cells was confirmed by real time RT-PCR, which detected expression of many neuronal markers, including CD133, nestin, microtubule-associate protein II, GABA receptor, NR4A2, N-cam, tyrosine hydroxylase, neurofilament, and Tau.

Further, a SB cell population from blood was induced to differentiate into adipocytes or osteogenic cells, i.e., mesoderm cells. More specifically, SB cell populations from the blood of two donors, donor 29 and donor 32 were cultured in media A, B, C, D, and E sequentially. Then, the medium was replaced by an adipocyte differentiation medium (Invitrogen) for 8 weeks. The adipocytes were stained using Oil-red-O and detected in an OD490 ELISA spectrophotometer. Donor 29 had an unusual high cell count of the SB cell population, which resulted in a high count of adipocytes. Alternatively, the medium was replaced by an osteogenesis medium (Invitrogen). Osteogenic cells were observed 2-4 weeks after the medium replacement. Osteogenic cells were stained with Alizarin Red, and detected by extracting from the cells Alizarin Red, which was measured at OD 405 nm in a spectrophotometer.

For induction to other mesoderm cells, stem cells in a SB cell population were cultured in the medium that contained 10 nM glucocorticoid and 10% FBS. After 1-month treatment, RNA was extracted from the cells, and expression of several genes was determined by Real Time PCR. Detectable expression of myosin heavy chain and skeletal myosin light chain indicates that stem cells in a SB cell population were differentiated to cardiomyocyte and skeletal muscle cells.

A SB cell population, like ES cells, could proliferate/grow on top of MEF feeder cells and form sphere on them. Also, like ES cells, under similar conditions, a SB cell population could give rise different typed of cells and form zygote like structures of self-cleavages of cells.

The above results suggest that a SB cell population is normally quiescent in tissues. Upon receipt a signal, e.g., an injury, they are activated and differentiate into suitable tissues to repair the damaged tissues. Thus, a SB cell population contains adult pluripotent stem cells and can be used for gene therapy, gene banking, drug screening, and creating universal donor cells. Also, these cells could be used to treat degenerative diseases, autoimmune diseases, or cancer.

EXAMPLE 3

Assays were carried out to examine the role of divalent cation chelating agent EDTA on stem cells in a SB cell population, including SB-1 cells.

Briefly, SB cell populations were obtained from a subject using an EDTA tube and a heparin tube, respectively, in the manner described in Example 1 above. The numbers of SB cells in the two populations were determined by a standard method. The results are shown below:

|  | SB cells |
|---|---|
| EDTA tube | 200 × 10$^6$/ml |
| Heparin tube | 10 × 10$^6$/ml |

The percentages of cells/particles of 1-6.0 µm in an EDTA tube and a heparin tube were about 5.8% and 0.2%, respectively. The results suggest that EDTA increased the number of SB-1 cells.

Further, a SB cell population prepared with the heparin tube was divided into two samples. One was incubated with an EDTA-containing medium ("Heparin+EDTA"); the other was incubated with EDTA-free control medium ("Heparin"). After 3 days of culturing, the ratio of small cells (<3 µm) in the two samples were determined. The ratio of large cells (>3 µm) in the two samples were also obtained. The results are shown below:

|  | "Heparin + EDTA":"Heparin" |
|---|---|
| Small Cells | 161:40 |
| Large Cells | 10:8 |

These results demonstrate that, in the presence of EDTA, the number of small cells in a SB cell population increased by more than 300% (161:40); in contract, the number of the large cells (i.e., non-SB cells) increased by only 25% (10:8).

Cell cytomety data from one subject also demonstrated that EDTA increased CD9+/SB-1 cells' numbers in a sample from 39.5% to 65.1% in the above-mentioned P3 gated region of the SB cell population. In contrast, a SB cell population prepared using a heparin tube had much higher percentages of the cells that are SSEA1+ and CD66e+, i.e., 2-10%.

The increase in the cell/particle number in the EDTA tube was possibly due to an increase in the number of platelets and microparticles. Indeed, EDTA can prevent platelets and microparticles from forming aggregation, which would precipitate. To rule out this possibility, a SB cell population prepared from the heparin tube was incubated with EDTA for 48-72 hours before cell cytomety was conducted. It was found that the increase in the particle number was almost from the stem cells, the sizes of which were in the range between 1 µm and 6.0 µm. The cell number increased by 50%.

To further purify the CD9+ cells (or to remove the platelets and microparticles), a SB cell population prepared from an EDTA tube was incubated with ADP for about 24 hours. It was found that CD9+CD349+ cells were further enriched by this ADP incubation. CD9+CD349+ cells accounted for 15.9% of the cells in the above-mentioned P3-gated region of the SB cell population that had been incubated with ADP; in contrast, CD9+CD349+ cells only accounted for 9.9% of the cells in the above-mentioned P3-gated region of the SB cell population that had not been incubated with ADP.

The results also show that EDTA specifically increased the number of SB-1 cells, which were smaller than 6.0 µm and stained positive for CD9+, not CD66e+ or SSEA4+ cells. The mechanism relates to that EDTA's ability to repress p53's function (presumably by chelating Zn++), thereby allowing stem cells to exist from the G0 quiescence stage and to enter the cell cycle 01. As the p53 protein requires Zn++ to fold properly and form a functional protein, chelating Zn++ by EDTA would be a key step to activate the stem cells. It is possible that EDTA can chelate other divalent ions and thereby activates stem cells that are in G0 phase and forces the stem cells to proliferate and expand.

EXAMPLE 4

As discussed below, determining the cell count of the SB cell population can be used to evaluate a subject's risk of having an ageing-related disorder or cancer.

According to flow cytometry, two healthy men who were more than 50 years old both had percentages of CD349+ cells in the above-mentioned P3-gated region of the SB cell population lower than 15%, i.e., 12.0% and 4.2%, respectively. In contrast, the percentages of CD349+ cells in the SB cell population in two healthy men younger than 25 were both higher than 15%, i.e., 18.6 and 22.9%, respectively. These results show that young healthy subjects each have a relative higher cell count of the SB cell population, as compared with that in old healthy subjects. This age-related decrease compromises the subject's stem cell-based abilities, including the ability to repair tissue after an injury.

As also determined by flow cytometry, SSEA4+ cells accounted for 35.6% of the cells in the above-mentioned P3-gated region of the SB cell population isolated from a young cancer survivor. This cell count is much higher than the average of a group of healthy young people. Based on this higher-than-average SSEA4 content, it is predicted that this subject has an excellent ability to repair injure tissue and a high risk of develop cancer. This evaluation is corroborated by (1) the subject's history of good repair ability, including quick recoveries from an eye Lasik surgery and an abdomen surgery and by (1) the subject's history of cancer. The similar evaluation can be made using the CD9+ cells disclosed herein.

The above results suggest that stem cells (e.g., SSEA4+ cells/SB-2 or CD9+/SB-1 cells) in a SB cell population, prepared using the above-described heparin tube, can be used as a biomarker for in vivo drug screening, prognosis for recovering from an injury or an infection, and cancer diagnosis. A high level of the SSEA4+ or CD9+ cells indicate that a subject has a young developmental status with a better ability to repair tissue damage, recover from an injury, and defend pathogens. On the other hand, it is positively correlated with a higher risk of having cancer.

EXAMPLE 5

In an in vivo cell tracking assay, 10$^6$ cells from a SB cell population, isolated from a human bone marrow sample, were injected intravenously to the tail of a SCID mouse (experimental SCID mouse). As a control, PBS was injected intravenously to the tail of a SCID mouse (control SCID mouse). After 30, 60, and 90 days, bone marrow, blood, and muscle were collected from both experimental and control SCID mice. The mouse bone marrow samples were analyzed using flow cytometry. The results show that MSC markers (i.e., human CD105, EGF receptor, Stro1, and CXCR1), a BLSC marker (i.e., CEA), and a very small embryonic-link stem cell (VSEL) marker (i.e., CD133) were detected by flow cytometry in the experimental SCID mouse, but not in the control SCID mouse. These results suggest that BLSCs, VSELs, and MSCs are down stream of the stem cells in a SB cell population. In addition, RNA extracted from the mouse muscle samples was analyzed by RT-PCR. Human myogenic factor 4, SM22, Pax7, and GAPDH were detected by real time RT-PCR. All primers used for detecting muscle markers with real time RT-PCR are listed below:

```
GADPH
                                           (SEQ ID NO: 15)
F: 5'-GAGTCAACGGATTTGGTCGT-3'

(SEQ ID NO: 16)
R: 5'-TTGATTTTGGAGGGATCTCG-3'

PAX7
                                           (SEQ ID NO: 61)
F: 5'-CGACTCCGGATGTAG AGA AA-3'

(SEQ ID NO: 62)
R: 5'-TTC CCG AAC TTG ATT CTG AG-3'
```

```
-continued
Myogenin factor 4 (skeletal)
                                           (SEQ ID NO: 63)
F: 5'-CAGTGCCATCCAGTACATCG-3'

(SEQ ID NO: 64)
R: 5'-AGGTTGTGGGCATCTGTAGG-3'

SM22 (Transgelin)
                                           (SEQ ID NO: 65)
F: 5'-TGATTCTGAGCAAGCTGGTG-3'

(SEQ ID NO: 66)
R: 5'-CGGTAGTGCCCATCATTCTT-3'
```

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

---

What is claimed is:

1. A method of generating muscle cells in a subject, the method comprising:
   obtaining from a subject a bodily fluid sample containing a plurality of cells,
   incubating the sample with EDTA or heparin in a container until the sample is separated into an upper layer and a lower layer,
   collecting the upper layer,
   isolating from the upper layer a population of somatic stem cells that are CD133− and 0.3-6.0 micrometers in size, and
   administering to a subject in need thereof an effective amount of the somatic stem cells, whereby the somatic stem cells differentiate into muscle cells in the subject.

2. The method of claim 1, wherein the somatic stem cells include CD9+, CD90−, and CD34− cells.

3. The method of claim 2, wherein the sample is a human blood or bone marrow sample.

4. The method of claim 1, wherein the administering step is performed by injecting the cells to the subject intravenously.

5. The method of claim 4, wherein the effective amount of the cells is $1 \times 10^6 \sim 10^{11}$ cells per injection.

6. The method of claim 4, wherein the sample is a human blood or bone marrow sample.

7. The method of claim 1, wherein the sample is a human sample.

8. The method of claim 7, wherein the sample is obtained from the subject.

9. The method of claim 8, wherein the sample is a blood or bone marrow sample.

10. The method of claim 1, wherein the sample is a blood or bone marrow sample.

11. A method of generating muscle cells, the method comprising:
    obtaining a bodily fluid sample containing a plurality of cells,
    incubating the sample with EDTA or heparin in a container until the sample is separated into an upper layer and a lower layer,
    collecting the upper layer,
    isolating from the upper layer a population of somatic stem cells that are CD133− and 0.3-6.0 micrometers in size, and
    culturing the somatic stem cells under conditions suitable for muscle cell differentiation, whereby muscle cells are generated.

12. The method of claim 11, wherein the somatic stem cells include CD9+, CD90−, and CD34− cells.

13. The method of claim 12, wherein the sample is a human blood or bone marrow sample.

14. The method of claim 11, wherein the somatic stem cells include SSEA1+, SSEA4+, CD13+, or Stro1+ cells.

15. The method of claim 14, wherein the sample is a human blood or bone marrow sample.

16. The method of claim 11, wherein the sample is a human sample.

17. The method of claim 16, wherein the sample is a blood or bone marrow sample.

* * * * *